United States Patent [19]

Schneider et al.

[11] 4,229,360

[45] Oct. 21, 1980

[54] PROCESS FOR THE DEHYDRATION OF A COLLOIDAL DISPERSION OF LIPSOMES

[75] Inventors: Michel Schneider, Grand-Lancy; Bernard Lamy, Carouge, both of Switzerland

[73] Assignee: Battelle Memorial Institute, Carouge, Switzerland

[21] Appl. No.: 931,243

[22] Filed: Aug. 4, 1978

[30] Foreign Application Priority Data

Aug. 5, 1977 [CH] Switzerland .................. 9615/77

[51] Int. Cl.³ .................. A23J 7/00; C07F 9/02; C11C 3/00
[52] U.S. Cl. .................. 260/403; 252/316; 424/36; 424/178; 424/199
[58] Field of Search .................. 260/403; 426/98, 99, 426/385, 663; 252/316; 424/36, 178, 199

[56] References Cited

U.S. PATENT DOCUMENTS

| | | | |
|---|---|---|---|
| 2,658,020 | 11/1953 | Schoch | 260/403 |
| 3,012,888 | 12/1961 | Davis | 426/662 |
| 3,041,289 | 6/1962 | Katchen | 252/316 |
| 3,060,030 | 10/1962 | Obenauf | 426/99 |
| 3,549,382 | 12/1970 | Hansen | 426/662 |
| 3,957,971 | 5/1976 | Oleniacz | 424/319 |
| 4,016,100 | 4/1977 | Suzuki | 424/19 |
| 4,089,801 | 5/1978 | Schneider | 252/316 |

Primary Examiner—John F. Niebling
Attorney, Agent, or Firm—Finnegan, Henderson, Farabow, Garrett & Dunner

[57] ABSTRACT

The invention concerns a process for the dehydration of a colloidal dispersion of liposomes in an aqueous liquid medium, this process being aimed at extending the conservation of the liposomes and to enable their efficient use at a later date.

According to this process, there is prepared a mixture of a hydrophilic compound and the liposome dispersion. This mixture is then subjected to a dehydration operation leading to the formation of liposomes in the form of a stable powder which can be stored for a long period and from which a dispersion of liposomes can be reconstituted.

5 Claims, No Drawings

PROCESS FOR THE DEHYDRATION OF A COLLOIDAL DISPERSION OF LIPSOMES

The present invention concerns the conservation of liposomes which are in the form of a colloidal dispersion in an aqueous medium.

As already known, the term "liposome" is currently used to call some microscopic vesicles which contain a liquid and the walls of which are formed from lipids of general formula XY, wherein X is a polar hydrophilic group and Y is a non-polar hydrophobic group.

The following groups can be mentioned as examples of polar groups X: phosphato, carboxy, sulfato, amino, hydroxy and choline. Examples on non-polar groups Y are: saturated or unsaturated hydrocarbons such as alkyl, alkenyl and alkynyl substituents which may possibly be substituted by a cyclo-alkyl radical.

As further known, liposomes are much advantageous for encapsulating biologically active substances. In this case, they may advantageously be formed from phospholipids such as lecithin, phosphatidyl-ethanolamine, phosphatidyl-serine or phosphatidic acid, for example.

However, because the liposome dispersions have a rather short and ill-known storage life, it is generally necessary to put them into use during the first months after preparation in order to avoid undesirable modifications in the course of time.

Thus, despite the many potential interesting applications of the liposomes, the use thereof has been limited by their relatively short storage life.

It would therefore be desirable to increase the conservation period of the liposomes and thus broaden their many applications in the encapsulation field. However, because of the relatively unstable structure of the liposomes, such conservation is connected with the solving of important practical problems. An object of the present invention is to markedly increase the conservation period of the liposomes and to maintain them in a stable condition from which they can be used, efficiently, at a later date.

Thus, an object of the present invention is a process for the dehydration of a liposome colloidal dispersion in an aqueous liquid medium, which comprises mixing a hydrophilic compound with the liposome dispersion and subjecting the obtained mixture to a dehydration operation leading to the formation of liposomes in the form of a stable powder which can be stored for a long period and from which, and with an aqueous medium, a liposome dispersion can be reconstituted.

Preferably, the dehydration will be carried out by lyophilisation (freeze-drying) which consists in subjecting said mixture to freezing followed by reduced pressure evaporation. Thus, the aqueous medium can be separated from the liposome vesicles by going directly from the solid to the gaseous state, the liposomes, therefore, not being subjected to any rough treatment and, thus, possible damages being avoided.

The liposome powder thus obtained is very stable during storage at room temperature and under moisture protection in a closed container, for instance in a vacuum-sealed package. This powder can be stored for a long period and, thereafter, reused by redispersing in a suitable aqueous medium in order to reconstitute a liposome dispersion.

Now, the dehydration operation is, in itself, not sufficient to practically implement the process of the invention and the initial mixing with a hydrophilic compound is a must. Effectively, it has been shown from experiments that the simple dehydration by lyophilisation of the liposome dispersion results in the formation of an oily sticking residue which is practically insoluble in water afterwards and which is thus useless for the reconstitution of a liposome dispersion suitable for usual liposome application. Consequently, the process of the invention not only enables a prolonged storage of the liposomes but, simultaneously, ensures that they are under a form suitable for recovery and further uses.

The hydrophilic compound used for carrying out the process of the invention can be advantageously selected among various high molecular weight compounds. For instance, very satisfactory results have been obtained with different hydrophilic polymers such as dextran, ox-albumin, polyvinyl alcohol (PVA), polyvinyl-pyrrolidone and gum arabic. Lower molecular weight compounds, such as sucrose can also be used. Therefore, said hydrophilic compound is actually a stabilizing additive which protects the liposomes of the dehydrated product and keeps them in a condition suitable for further use. Further, the presence of such a hydrophilic compound in the liposome powder is not likely to cause any particular inconvenience, especially if natural polymers chosen among those described above are used. Thus, when dextran is used, any kind of subsequent use of the liposome powder according to the invention can be contemplated.

In the cases where the liposomes thus preserved should be injected into the blood system, polyvinyl-pyrrolidone or dextran will preferably be used as the hydrophilic compound. Conversely, if the liposomes must be administered orally, it is possible to use all the hydrophilic compounds exemplified above.

The amount of said hydrophilic compound to be mixed with the liposome dispersion before dehydration will preferably be equal to the quantity of the substance making the liposome walls of said dispersion. However, this quantity of hydrophilic compound is not critical and can be varied within wide limits when using different embodiments of the invention.

The following Examples illustrate the invention in more details.

EXAMPLE 1

A liposome dispersion in water was prepared which comprised 25 mg of lecithin per ml of dispersion; the encapsulated solution was a 100 mg/ml aqueous insulin solution. Dextran (Pharmacia T-70) (25 mg/ml) was added as a stabilizer to the liposome dispersion and was thoroughly mixed therein. The liquid mixture was placed at $-30°$ C. for an hour after which it had solidified, then it was subjected to a reduced pressure of 0.1 Torr which caused the sublimation of the ice in a few hours.

The fine lyophilized powder thus obtained was stored under vaccum for a period of time. One hundred mg samples were taken at intervals, the first right after lyophilisation, the others after a fortnight, 1 month, 2 months, 6 months, 1 year and 1.5 years of storage period. These samples were easily dispersed in water and thus provided reconstituted dispersions of liposomes. Said dispersions were subjected to ultrafiltration in order to retain the liposomes and determine the amount of undamaged vesicles by titrating the free insulin of the filtrate and substracting the value from the total insulin of the dispersion. The results, recorded in Table I below, indicate that about 30% of the liposomes were destroyed initially during lyophilisation. On the other hand, the undamaged liposomes of the lyophilized powder did not undergo any significant degradation even after 1.5 year storage time.

TABLE I

| Liposome condition (storage time) | % of undamaged liposomes |
|---|---|
| Initial dispersion | 100 |
| Immediately after dehydration | 68.2 |
| 15 days | 71.5 |
| 1 month | 64.8 |
| 6 months | 66.6 |
| 1 year | 70.4 |
| 1.5 years | 65.2 |

The observed variations (±5%) around the average value are within the margin of measurement errors.

EXAMPLE 2

There was proceeded as described in Example I above with the difference that dextran was replaced by an equal weight of gum arabic as stabilizer. After dehydration, the lyophilized powder contained 71.5% of the liposomes of the original colloidal dispersion. After two month storage, this value was still 70.2%, i.e. the storage period had caused no significant damage to the liposomes.

Other comparative experiments were run on the storage life of liposomes according to the invention and according to the procedures of Examples 1 and 2 above and using, respectively as stabilizers, ox-albumin, gum arabic, dextran, polyvinyl alcohol (PVA) and polyvinyl-pyrrolidone (PVP). The weight ratios of stabilizers to the lecithin of the liposomes was 1:1 on one series of cases and 4:1 in another series of cases. The results from these experiments showed that all stabilizers behaved about similarly and that increasing the amount thereof relatively to the liposomes improved the conservation results. For instance, in the 4:1 ratio series, the recovery level after lyophilization went up to 76.2% of undamaged liposomes (stabilizer, gum arabic).

The above discussion shows that the process of the invention can be worked relatively simply and rapidly. The dehydration by lyophilization, as disclosed, is particularly advantageous since it is a careful processing which causes only a small percentage loss of the liposomes subjected thereto. It is however possible to contemplate other dehydration means, e.g. drying in the presence of air at moderate temperature in order to prevent destroying the liposomes by heat.

What we claim is:

1. A process for the dehydration of a colloidal dispersion of liposomes in an aqueous liquid medium, which comprises mixing a hydrophilic compound with the liposome dispersion and dehydrating the mixture to form a stable liposome containing powder which can be stored and reconstituted in an aqueous medium as a liposome dispersion.

2. The process of claim 1, in which the mixture is dehydrated by first freezing said mixture of the liposome dispersion and the hydrophilic compound and, thereafter, removing water from said frozen mixture by reduced pressure evaporation to obtain said powder of liposomes.

3. The process of claims 1 or 2, wherein the liposomes consist essentially of vesicles of a liquid encapsulated in a film of a lipid and said mixture includes, by weight, at least as much of the hydrophilic compound as of the lipid used to form the liposomes.

4. The process of claim 3 wherein the weight ratio of the hydrophilic compound to the lipid is from 1 to 1 to 4 to 1.

5. The process of claim 3, wherein said hydrophilic compound is selected from the group comprising dextran, gum arabic, polyvinyl alcohol, polyvinyl pyrrolidone and ox-albumin.

* * * * *

REEXAMINATION CERTIFICATE (1585th)
United States Patent [19]

Schneider et al.

[11] B1 4,229,3

[45] Certificate Issued  Nov. 5, 19

[54] PROCESS FOR THE DEHYDRATION OF A COLLOIDAL DISPERSION OF LIPOSOMES

[75] Inventors: Michel Schneider, Grand-Lancy; Bernard Lamy, Carouge, both of Switzerland

[73] Assignee: Liposome Company, Inc.

Reexamination Request:
No. 90/002,252, Jan. 11, 1991

Reexamination Certificate for:
Patent No.: 4,229,360
Issued: Oct. 21, 1980
Appl. No.: 931,243
Filed: Aug. 4, 1978

[51] Int. Cl.$^5$ .......................... A23J 7/00; C07F 9/02; C11C 3/00
[52] U.S. Cl. .................................. 260/403; 252/316; 424/36; 424/178; 424/199
[58] Field of Search ................. 264/4.6; 424/450, 491, 424/498; 426/385, 663, 989; 252/316

[56] References Cited
PUBLICATIONS

Sreter et al., 1970, Biochim Biophys Acta 203:354–:
Racker, 1972, J. Memb. Biol 10:221–35.
Hinkle et al., 1972, J. Biol. Chem. 247(4):1338–39.
Darnell, et al., Molecular Cell Biology, Scient American Books, Inc. 1986, pp. 887–890.

*Primary Examiner*—John F. Niebling

[57] ABSTRACT

The invention concerns a process for the dehydratior a colloidal dispersion of liposomes in an aqueous liq medium, this process being aimed at extending the c servation of the liposomes and to enable their effici use at a later date.

According to this process, there is prepared a mixt of a hydrophilic compound and the liposome disp sion. This mixture is then subjected to a dehydrati operation leading to the formation of liposomes in form of a stable powder which can be stored for a lo period and from which a dispersion of liposomes can reconstituted.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-3 are determined to be patentable as amended.

Claims 4-5, dependent on an amended claim, are determined to be patentable.

New claims 6-15 are added and determined to be patentable.

1. A process for the dehydration of a colloidal dispersion of liposomes [in an aqueous liquid medium] which comprises mixing a hydrophilic compound with [liposome dispersion] *colloidal dispersion of the liposomes in an aqueous liquid medium,* and dehydrating the mixture to form a stable [liposome containing] powder which can be stored and reconstituted in an aqueous medium [as a liposome dispersion] *to recover* *colloidal dispersion of liposomes which is suitable for administration in vivo.*

2. The process of claim 1, in which the mixture is [hydrated] *dehydrated* by first freezing said mixture of the liposome dispersion and the hydrophilic compound and, thereafter, removing water from said frozen mixture by reduced pressure evaporation to obtain said powder [containing liposomes].

3. The process of claim 1 or 2, wherein the liposomes consist essentially of vesicles of a liquid encapsulated in [a film of a] *a* lipid *bilayer* and said mixture includes, by weight, at least as much of the hydrophilic compound as of the lipid used to form the liposomes.

6. *A process for the dehydration of a colloidal dispersion of liposomes, which comprises mixing a hydrophilic compound with the colloidal dispersion of the liposomes in an aqueous liquid medium, and dehydrating the mixture to form a stable powder which can be stored and reconstituted in an aqueous medium to recover the colloidal dispersion of liposomes which is suitable for oral administration.*

7. *The process of claim 6, in which the mixture is dehydrated by first freezing said mixture of the liposome dispersion and the hydrophilic compound and, thereafter, removing water from said frozen mixture by reduced pressure evaporation to obtain said powder.*

8. *The process of claims 6 or 7, wherein the liposomes consist essentially of vesicles of a liquid encapsulated in a lipid bilayer and said mixture includes, by weight, at least as much of the hydrophilic compound as of the lipid used to form the liposomes.*

9. *The process of claim 8 wherein the weight ratio of the hydrophilic compound to the lipid is from 1 to 1 to 4 to 1.*

10. *The process of claim 8, wherein said hydrophilic compound is selected from the group comprising dextran, gum arabic, polyvinyl alcohol, polyvinyl pyrrolidone and ox-albumin.*

11. *A process for the dehydration of a colloidal dispersion of liposomes, which comprises mixing a hydrophilic compound with the colloidal dispersion of the liposomes in an aqueous liquid medium and dehydrating the mixture to form a stable powder which can be stored and reconstituted in an aqueous medium to recover the colloidal dispersion of liposomes which is suitable for injection into a patient.*

12. *The process of claim 11, in which the mixture is dehydrated by first freezing said mixture of the liposome dispersion and the hydrophilic compound and, thereafter, removing water from said frozen mixture by reduced pressure evaporation to obtain said powder.*

13. *The process of claims 11 or 12, wherein the liposomes consist essentially of vesicles of a liquid encapsulated in a lipid bilayer and said mixture includes, by weight, at least as much of the hydrophilic compound as of the lipid used to form the liposomes.*

14. *The process of claim 13 wherein the weight ratio of the hydrophilic compound to the lipid is from 1 to 1 to 4 to 1.*

15. *The process of claim 13, wherein said hydrophilic compound is selected from the group comprising dextran, gum arabic, polyvinyl alcohol, polyvinyl pyrrolidone and ox-albumin.*

* * * * *